(12) United States Patent
Eidt et al.

(10) Patent No.: US 11,597,901 B2
(45) Date of Patent: Mar. 7, 2023

(54) ADAPTER FOR CELL-CULTURE VESSEL

(71) Applicants: Bayer Aktiengesellschaft, Leverkusen (DE); Bayer Healthcare LLC

(72) Inventors: Annette Eidt, Odenthal (DE); Wolf Kloeckner, Cologne (DE); Helmut Brod, Cologne (DE); Martin Poggel, Cologne (DE); Bernd Tscheschke, Cologne (DE)

(73) Assignees: Bayer Aktiengesellschaft, Leverkusen (DE); BAYER HEALTHCARE LLC, Whippany, NJ (US)

( * ) Notice: Subject to any disclaimer, the term of this patent is extended or adjusted under 35 U.S.C. 154(b) by 541 days.

(21) Appl. No.: 16/318,109

(22) PCT Filed: Jul. 19, 2017

(86) PCT No.: PCT/EP2017/068214
§ 371 (c)(1),
(2) Date: Jan. 15, 2019

(87) PCT Pub. No.: WO2018/019675
PCT Pub. Date: Feb. 1, 2018

(65) Prior Publication Data
US 2021/0277346 A1 Sep. 9, 2021

(30) Foreign Application Priority Data
Jul. 29, 2016 (EP) ..................... 16181914

(51) Int. Cl.
*C12M 1/24* (2006.01)
*C12M 1/00* (2006.01)

(52) U.S. Cl.
CPC ............ *C12M 23/08* (2013.01); *C12M 23/38* (2013.01)

(58) Field of Classification Search
None
See application file for complete search history.

(56) References Cited

U.S. PATENT DOCUMENTS 4,184,916 A * 1/1980 Tolbert ................ B01D 29/11
435/297.2
5,817,505 A * 10/1998 Thompson ......... B01D 21/0045
435/286.1

(Continued)

FOREIGN PATENT DOCUMENTS

EP          1591517 A1    11/2005
WO     2012076442 A1     6/2012

(Continued)

OTHER PUBLICATIONS

Klockner et al., Shake-Flask Bioreactors, Chapter 2.17 of Comprehensive Biotechnology (Second Edition), vol. 2, 2011, pp. 213-226 (Year: 2011).*

(Continued)

*Primary Examiner* — Holly Kipouros
(74) *Attorney, Agent, or Firm* — McBee Moore & Vanik IP, LLC

(57) ABSTRACT

Disclosed herein is a sterilizable adapter for a cell culture vessel comprising a body, an upper connection and/or a lid, at least one port, a ventilation passage, a lower internal connection suitable for connection to a cell culture vessel and a cell retention device and/or a cell separation device as well as a device comprising said sterilizable adapter and a method for cell cultivation using said sterilizable adapter.

9 Claims, 10 Drawing Sheets

(56) References Cited

U.S. PATENT DOCUMENTS

| | | |
|---|---|---|
| 9,809,792 B2 | 11/2017 | Kauling et al. |
| 9,840,691 B2 | 12/2017 | Pastor et al. |
| 2005/0130291 A1 | 6/2005 | Erhardt et al. |
| 2015/0017716 A1 | 1/2015 | Kauling et al. |
| 2015/0024478 A1 | 1/2015 | Pastor et al. |
| 2015/0218501 A1 | 8/2015 | Kauling et al. |
| 2016/0215257 A1* | 7/2016 | Davis ............... C12M 47/00 |

FOREIGN PATENT DOCUMENTS

| | | |
|---|---|---|
| WO | 2013124326 A1 | 8/2013 |
| WO | 2013124329 A1 | 8/2013 |

OTHER PUBLICATIONS

Iding et al., Influence of alterations in culture condition and changes in perfusion parameters on the retention performance of a 20 μm spinfilter during a perfusion cultivation of a recombinant CHO cell line in pilot scale, 2000, Cytotechnology, 34, pp. 141-150 (Year: 2000).*

Tyo et al., Novel high density perfusion system for suspension culture metabolic studies, paper presented at 1989 AIChE Annual Meeting, Nov. 5-10, 1989.*

International Search Report issued in counterpart Application No. PCT/EP2017/068214, dated Oct. 13, 2017.

Meier, et al., "Quasi-continuous fermentation in a reverse-flow diafiltration bioreactor," Biochemical Engineering Journal, (2014), vol. 91: 265-275.

\* cited by examiner

ADAPTER FOR CELL-CULTURE VESSEL

CROSS-REFERENCE TO RELATED APPLICATIONS

This application is a National Stage entry of International Application No. PCT/EP2017/068214, filed Jul. 19, 2017, which claims priority to European Patent Application No. 16181914.9, filed Jul. 29, 2016.

BACKGROUND

Field

The invention relates to a sterilizable adapter for a cell culture vessel comprising at least one port acting as inlet and/or as outlet of preferably liquid or gaseous substances allowing for cultivation of microorganisms and cell cultures in a cell culture vessel under controlled culture conditions using batch, fed-batch, repeated fed-batch and/or continuous cultivation conditions e.g. perfusion culture conditions.

Description of Related Art

In the cultivation of microorganisms and cell cultures, in particular of animal, plant and human cells, various types of bioreactors are used.

In commercial biotechnological processes cell cultivation is typically performed in large, fully equipped bioreactors under controlled conditions in terms of pH, dissolved oxygen concentration, liquid level, temperature and offgas analysis. Fully equipped bioreactors offer ports for feeding of nutrient solutions, addition of acid and base for pH control or antifoam agents as well as ports for sampling or continuous removal of cell suspension or fermentation broth. Controlled conditions in terms of pH, temperature and oxygen supply ensure comparability between different cell culture runs as well as reproducibility, which is important for a consistent and reliable product quality. Depending on the cell type and the process to be developed and optimized, batch, fed-batch, repeated fed-batch, perfusion and/or continuous cultivation conditions e.g. perfusion culture conditions are required.

During the development and optimization of such biotechnological processes a plurality of parameters—such as cell lines, media, and feeds—need to be altered and adjusted in order to enhance product quality and production efficiency.

When altering and adjusting the individual parameters in order to optimize the cell culture conditions either a great number of bioreactors are needed or the individual parameters can only be analyzed one after another, resulting in an very long in-efficient process development time. Moreover, in both scenarios each parameter to be tested requires the set-up of a complete, fully equipped cell culture bioreactor resulting in extremely high costs especially in the case of continuous culture conditions.

Therefore, there is a need for a simplified system that allows a faster, more efficient and cost reduced process-development ideally with the functionality of a fully equipped bioreactor in terms of process control, feeding, sampling and monitoring.

SUMMARY

It was surprisingly found that this objective can be achieved by providing a sterilizable adapter for a cell culture vessel as described below.

Thus in a first aspect herein is provided a sterilizable adapter for a cell culture vessel comprising a body, an upper connection and/or a lid, at least one port, a ventilation passage, a lower internal connection suitable for connection to a cell culture vessel and a cell retention device and/or a cell separation device.

In a second aspect a device is provided comprising a sterilizable adapter as described above, a cell culture vessel and a lid.

In another aspect the use of the device described above is provided herein.

In still another aspect a cell cultivation method is provided herein using a sterilizable adapter as described above and/or a device as described above.

BRIEF DESCRIPTION OF THE DRAWINGS

The skilled artisan will understand that the drawings, described below, are for Illustration purposes only. The drawings are not intended to limit the scope of the present invention.

DETAILED DESCRIPTION OF A PREFERRED EMBODIMENT

Figure 1:
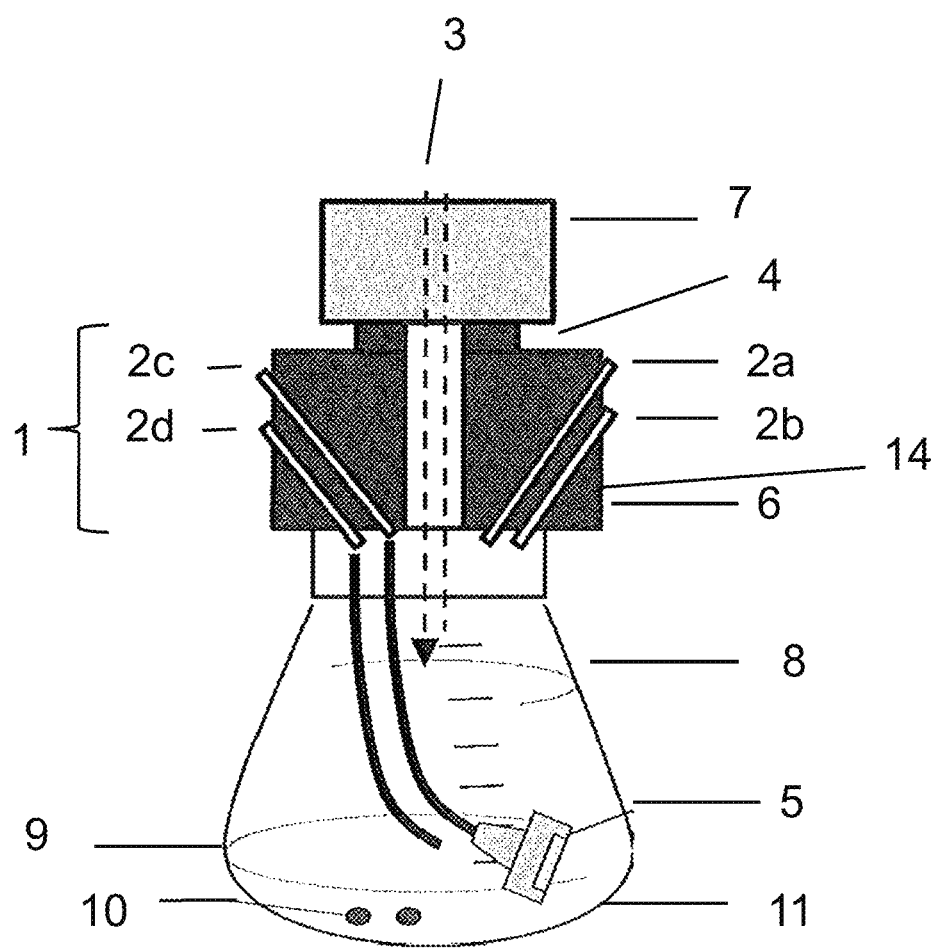
FIG. 1 shows a schematic overview of a device comprising a sterilizable adapter and a cell retention device.

It is to be understood that the terminology used herein is for the purpose of describing particular embodiments only, and is not intended to be limiting. As used in this specification and the appended claims the words "a" and "an" denote "one or more."

Provided herein is a sterilizable adapter for a cell culture vessel comprising a body, an upper connection and/or a lid, at least one port, a ventilation passage, a lower internal connection suitable for connection to a cell culture vessel and a cell retention device and/or a cell separation device.

Using this sterilizable adapter in combination with a standard cell culture flask allows for cell cultivation under continuous culture conditions e.g. perfusion culture conditions. In addition, also fed-batch, repeated fed-batch and batch culture can be performed using the sterilizable adapter. In other words, via employing the sterilizable adapter it is possible to perform cell culture under reproducible and comparable conditions using standard cell culture vessels, which are more readily available, easier to handle and more cost-effective than fully equipped bioreactors.

Due to the small scale the costs for development and optimization of biotechnological processes are reduced since less culture media and material are needed and the requirements in terms of equipment and time spent on culture maintenance are minimized.

Moreover, the sterilizable adapter differs from devices known in the art inter alia, since the cell retention device and/or the cell separation device render the sterilizable adapter described herein suitable for small scale cell culture. Due to the cell retention device that retains the cells to be cultured within the cell culture vessel, continuous perfusion cell culture is feasible even on a small scale. The same argument applies, if a cell separation device optimized for small culture volumes is used. Thus, via employing the sterilizable adapter described herein, it is possible to perform cell culture under reproducible and comparable conditions allowing a faster, more efficient and cost reduced process-development possibly with the functionality of a fully equipped bioreactor in terms of process control, feeding, sampling and monitoring.

As used herein the term "batch" refers to a culture condition, in which no cell culture medium is added to the cell culture and no continuous removal of cell-culture medium takes place during cultivation. In other words, also under batch type culture conditions cell culture medium can be removed at different time points during cultivation e.g. during sampling.

As used herein the term "fed-batch" refers to a culture condition, in which cell culture medium is added to the cell culture during cultivation but no continuous removal of cell-culture medium takes place during cultivation.

As used herein the term "repeated fed-batch" refers to a fed-batch culture condition, in which the cell culture medium is periodically removed in part and nutrient solution is subsequently added.

For example the nutrient solution can be glucose containing solution and said nutrient solution is added until the original level of cell culture medium is reached again.

If the cell retention device and/or the cell separation device of the sterilizable adapter is not needed during cell culture under batch, fed-batch or repeated fed-batch conditions, it might—depending in the type of sterilizable adapter employed—simply be closed off or be removed from the sterilizable adapter.

As used herein the term "continuous" refers to a culture condition, in which solution such as cell culture medium is added to the cell culture and aspirated from the cell culture continuously during cultivation.

As used herein the term "perfusion" refers to a type of continuous cell culture, in which cell culture medium is added to the cell culture and removed from the cell culture continuously during cultivation. In order to maintain cell density levels, at least part of the cultured cells need to be retained in the cell culture vessel or separated from the removed medium under perfusion cell culture conditions. In case of a separation outside the cell culture vessel the cells will be returned to the cell culture vessel once they have been separated from the aspirated solution. In addition, under perfusion culture conditions a part of the cultured cells is typically discarded, i.e. not retained in the culture vessel or returned to it, in order to maintain a given target cell density and remove non-viable cells ("purge").

As used herein, the term "sterilizable" refers to the fact that the material in question can be made abacterial by a known method, such as autoclaving, gamma irradiation or chemical inactivation.

The body of the sterilizable adapter comprises least one material selected from the group consisting of stainless steel, synthetic and/or semi-synthetic materials such as polyether ether ketone (PEEK), poly tetra fluor ethylene (PTFE), poly vinylidene di fluoride (PVDF) or silicone elastomers.

In a preferred embodiment the body of the sterilizable adapter is made of polyether ether ketone (PEEK).

As used herein the term "upper connection" refers to the part of the device suited to be attached to a lid, e.g. to the original lid of the chosen cell culture vessel.

As used herein the term "lower internal connection suitable for connection to a cell culture vessel" refers to the part of the device suited to be attached to the cell culture vessel.

This attachment could be for example via insertion, bonding or screwing.

As used herein the term "ventilation passage" refers to a component allowing for the gas exchange between the gaseous phase inside the cell culture vessel and the upper connection or the lid of the sterilizable adapter and ultimately the surrounding atmosphere, e.g. an incubator or a temperature controlled culture room.

As used herein the term "port" or "connector" refers to an opening through which substances can be added to or removed from the inside of the cell culture vessel.

Hence, the ports serve as inlets and/or outlets and their shape, their exact position, their number and their size can vary depending on the experimental requirements.

As used herein the term "cell separation device" refers to a component, which separates the cells from the medium outside of the cell culture vessel. Thus, when using a cell separation device at least a part of the cells are usually returned to the cell culture vessel after separation in order to maintain cell density levels.

As used herein the term "cell retention device" refers to a component, which holds back the cells while allowing other substances such as cell culture medium to be removed from the cell culture vessel.

In other words the cell retention device either retains the cells in the culture medium present in the culture vessel or retains the cells after they have been aspirated together with the culture medium. However, also in the second case the cells do not leave the culture vessel. Instead cell retention i.e. cell removal from the medium is carried out within the culture vessel.

The use of a cell retention device can be combined with the use of a cell separation device.

Moreover, it is possible that more than one cell retention and/or cell separation device are employed.

Examples for a cell retention device are a piece of tubing made from e.g. synthetic, elastomeric or metal construction materials. Examples for a cell retention device in form of a piece of tubing made from synthetic construction material are a piece of plastic tubing or silicone rubber tubing. An example for a cell retention device in form of a membrane for cell retention is a membrane for cell retention made of e.g. hydrophilic polyethersulfone or polypropylene with a pore size between 0.1 µm and 10 µm or a pulsed diafiltration membrane.

In one embodiment the cell retention device in form of a metal piece of tubing is made of stainless steel.

The use of one kind of cell retention device can be combined with the use of one or more other cell retention devices of the same kind or of a different kind.

Employing a pulsed diafiltration membrane for cell retention is known in the art (cf. Meier et al. 2014). In the case of a shake flask the membrane of such a device would be carried along in the cell culture medium during rotation.

Preferably, the cell retention device retains more than 80%, even more preferably more than 90% and most preferably 100% of the cells that come into contact with the cell retention device.

The cell retention rate is calculated via determining the perfusion rate. The perfusion rate describes the amount of culture broth harvested compared to the total volume of culture in the fermenter. The units of perfusion rate are volumes/day. The harvest flow rate is in ml/min and the volume is in L (1.44 converts ml/min to L/day).

In units of volumes/day:

$$r_{perfusion} = \frac{1.44 F_H}{V}$$

Kwash

The $K_{wash}$ value describes the percentage of viable cells lost in the harvest in units of %:

$$K_{wash} = 100 \frac{n_H}{n_F}$$

The viable cell concentration in the harvest stream and in the bioreactor is specified with $n_H$ and $n_F$, respectively. $K_{wash,total}$ describes the percentage of total cells lost in the harvest.

In units of %:

$$K_{wash,total} = 100 \frac{n_{H,total}}{n_{F,total}}$$

The total cell concentration in the harvest stream and in the bioreactor is specified with $n_{H,total}$ and $n_{F,total}$, respectively. In order to determine the number of cells in a sample the cells can be counted with a commercially available cell counter such as the "Cedex HiRes Analyzer", Roche Innovatis, Germany.

The $K_{wash}$ value is preferably between 20%-0.1%, more preferably between 10%-0.1%, and most preferably between 2%-0.1%.

Depending on the cultured cells and the used cell culture vessel the geometry of the cell retention device can vary for example the cell retention device can be round or rectangular.

Accordingly, depending on the cultured cells and the used cell culture vessel the inner diameter, the length, the form and the shape of the cell retention device may vary.

Exemplary forms of cell retention devices—especially the forms of elastomeric, plastic or metal pieces of tubing acting as cell retention devices—are straight and/or bent and/or straight and inclined with an angle between 10° and 90°, more preferably with an angle between 60° and 80° and most preferably with an angle of 70°-75° with respect to a horizontal line.

In a preferred embodiment the piece of tubing acting as cell retention device is straight and inclined with an inclination angle between 40° and 80°.

Thus, these cell retention devices take advantage of gravity i.e. they are gravity cell settlers.

In other words, the sterilizable adapter for a cell culture vessel described herein is in one embodiment characterized in that the at least one cell retention device is a gravity cell settler.

Moreover, a cell retention device, especially a piece of tubing employed as cell retention device, can have a conical or cylindrical shape.

Furthermore, a cell retention device, especially a piece of tubing employed as cell retention device, can have an inner diameter between 2 mm and 20 mm, more preferably between 2 mm and 12 mm, most preferably between 3 mm and 10 mm.

In addition, a cell retention device, especially a piece of tubing employed as cell retention device, can have a length between 2 cm and 100 cm, more preferably between 10 cm and 40 cm and most preferably between 12 and 30 cm.

In a preferred embodiment the piece of tubing used as cell retention device has an inner diameter between 2 mm and 20 mm and a length of 30 cm.

Such a cell retention device is preferred, as it ensures a constant cell retention rate, it minimizes cell damage, it can be used over the whole cell culture period and it ensures that the retention time is adequate.

In another preferred embodiment the cell retention device made from elastomeric tubing is a piece of straight silicone tubing with a diameter of 4.8 mm and a length of 163 mm.

In a further preferred embodiment the cell retention device is manufactured from stainless steel, has a length of 20 cm-24 cm, an inner diameter of 8 mm-12 mm and is inclined with an angle of 70-75° with respect to a horizontal line.

This embodiment has the effect, that the cell retention device—here a gravity cell settler—facilitates perfusion cell culture in a small scale cell culture while obtaining and maintaining high cell densities.

These high cell densities are even obtained and maintained, if the cell culture vessel onto which the sterilizable adapter comprising this embodiment of a cell retention device is mounted, is a shake flask, i.e. the small scale cell culture is cultured under shaking culture conditions during constant orbital rotational movement. This is surprising, since—without wishing to be bound by theory—it was expected that the constant orbital rotational movement would interfere with cell sedimentation in cell retention devices working on the basis of gravity and hence it would not be possible to obtain and maintain high cell densities.

One example of this embodiment is a cell retention device manufactured from stainless steel with a length of 23.5 cm, an inner diameter of 10 mm and an inclination angle of 74° with respect to a horizontal line.

As used herein the term "small scale cell culture" refers to cell cultures with a cultivation volume of 1 ml to 500 ml.

Preferably, the small scale cell culture has a cultivation volume of 90 to 170 ml.

As used herein the term "high cell density" refers to a viable cell number of $10\text{-}80 \times 10^6$ cells/ml as well as the fact that the cell culture is started with a cell density below $10 \times 10^6$ cells/ml. Moreover, once the desired value of high cell density is reached it is substantially maintained throughout the entire cell culture period. In one embodiment, the high cell density cell culture has a viable cell number of $18\text{-}40 \times 10^6$ cells/ml.

The cell culture density depends on several factors for example the starting cell number, the growth rate of the cells, the rate at which culture medium is added and removed or the harvest cell rate. It can e.g. be measured daily, by withdrawing a sample from the culture and counting the cells with a cell counting device such as the Cedex HiRes. Alternatively or in addition, the cell culture density can be determined at the end of a cell culture period.

In one example the following cultivation conditions apply: viable cell number of $10\text{-}80\times10^6$ cells/ml in the cell culture vessel, a harvest cell rate of $0.01\text{-}5\times10^6$ cells/mL and a rate at which culture medium is added and removed of 0.05-1.5 l/h in relation to cell culture volume [volume/volume/h].

Typical cell culture periods are 4 to 8 weeks. Thus, it is important that the cell retention device does not need to be replaced during this time. Reasons for replacing a cell retention device are, inter alia, blocking or leakage.

Moreover, cell residence time, i.e. the time spend by the cells within the cell retention device, has to be adequate for a given cell type otherwise the cells might be damaged e.g. by being depleted of oxygen and/or nutrients or via aggregate formation.

Preferably, the cell separation device holds back more than 80%, even more preferably more than 90% and most preferably 100% of the cells that come into contact with the cell separation device.

Examples for cell separation devices are inclined-channel gravity settlers, filtration devices or centrifuges. Inclined-channel gravity settlers are referred to as "settlers" within this text.

In a preferred embodiment the cell separation device is a settler. In a particularly preferred embodiment, the settler is a pre-sterilized single-use settler made from thermoplastic and elastomeric materials of construction as described in WO2013124326 A1 and WO2013124329 A1.

This embodiment allows the separation of cells in small volumes outside of the cell culture vessel.

In one embodiment of the sterilizable adapter for a culture vessel described herein, the culture vessel is a shaker vessel also termed shake flask, i.e. a vessel suitable for culturing microorganisms, yeast, plant and animal cells while shaking.

In case that a shake flask is used for cultivation, the sterilizable adapter described herein overcomes the need to interrupt the shaking process for sampling, adding media or other components. Thus, the sterilizable adapter enables controlled and monitored cell culture conditions in shake flasks without interruption and hence ensures consistent culture conditions. These consistent culture conditions are a prerequisite for comparing different cell culture runs with each other and hence adjustment of individual parameters in order to optimize cell culture conditions.

Moreover, the parallel culture of several shake flasks with sterilizable adapters as described herein mounted on one shaking platform in one incubator considerably reduces cultivation costs and complexity, thus allowing for a faster, more efficient and cost reduced process-development yet under reproducible and comparable conditions.

Preferred shake flasks are Erlenmeyer flasks.

The shake flask is preferably shaken with, i.e. the shaking conditions are, 40 to 1000 rpm, more preferably with 100 to 500 rpm, most preferably with 80-120 rpm.

Moreover, preferably a shaking radius between 1 mm and 50 mm, more preferably between 15 mm and 35 mm most preferably with 25 mm is used.

Furthermore, preferably a shake flask with a total volume between 50 ml and 5000 ml, more preferably between 100 and 1000 ml, most preferably with 500 ml is employed.

Preferably the relative filling volume of a shake flask lies between 5% and 50% of the total volume of that shake flask more preferably between 10% and 30%, most preferably it is 20%.

In one embodiment the sterilizable adapter for a cell culture vessel described herein is a sterilizable adapter for a small-scale cell culture.

As stated above as used herein the term "small scale cell culture" refers to cell cultures with a cultivation volume of 1 ml to 500 ml.

Preferably, the small scale cell culture has a cultivation volume of 90 to 170 ml.

Most preferably the small scale cell culture has a cultivation volume of 100-145 ml.

As used herein the term "cultivation volume" refers to the total volume of nutrient solution present in the device comprising the sterilizable adapter and the cell culture vessel as well as in the cell retention and/or cell separation device.

Cell cultures with such a small volume allow a considerable reduction in costs for cell culture maintenance, i.e. costs of cell culture media, additional factors, personnel for handling the cultures and space requirements. Via employing the sterilizable adapter described herein, these small scale cell cultures combine the cost reduction with the possibility to reproducibly and reliably simulate the cell culture conditions in a conventional bioreactor, thereby enhancing data quality. This is important in order to be able to scale up the findings made in a small laboratory scale to standard production processes.

As stated above a sterilizable adapter comprising a cell retention device in form of a gravity cell settler manufactured from stainless steel, with a length of 20 cm-24 cm, an inner diameter of 8 mm-12 mm and an inclination angle of 70-75° with respect to a horizontal line is preferred when using a shake flask.

This embodiment has the effect, that the cell retention device facilitates perfusion cell culture in a small scale cell culture while obtaining and maintaining high cell densities.

These high cell densities are even obtained and maintained, if the cell culture vessel onto which the sterilizable adapter comprising this embodiment of a cell retention device is mounted is a shake flask, i.e. the small scale cell culture is cultured under shaking culture conditions during constant orbital rotational movement. This is surprising, since—without wishing to be bound by theory—it was expected that the constant orbital rotational movement would interfere with cell sedimentation in the cell retention device taking advantage of gravity and hence it would not be possible to obtain and maintain high cell densities.

Typically, several cell culture vessels on which sterilizable adapters are mounted, will be placed next to each other on a shaking platform.

Usually the cell culture vessel on which the sterilizable adapter is mounted will be cultured in an incubator, i.e. a device used to grow and maintain microbiological cultures or cell cultures, which maintains optimal temperature, humidity and other conditions such as the carbon dioxide ($CO_2$) and oxygen content of the atmosphere inside. However, other systems such as a controlled cultivation room, which maintains optimal temperature, humidity and other conditions such as the carbon dioxide ($CO_2$) and oxygen content of the atmosphere inside can also be used. In the case of shake flasks the shaker could be located in such a room.

The sterilizable adapter described herein is especially suited for mounting on a standard culture vessel such as a shake flask. This combination is suited for systems hosting several shake flask cultures, in which homogenization of the cells is ensured in parallel, which are well known in the art. Hence, in such a system setting and maintaining culture conditions such as temperature, carbon dioxide content, shaking frequency and shaking diameter only requires one central drive for agitation, one central temperature control, one ventilation control etc. Thus, such an arrangement is typically more cost-effective and time-saving compared to stirred bioreactors that require a separate stirrer drive, a temperature control, a gas supply, e.g. a sparger etc. for each bioreactor. Via using the sterilizable adapter the drawback of conventional shake flask cultures that each time, when a sample has to be withdrawn or a feed solution has to be added, the shaker has to be stopped and the culture vessels have to be taken out of the incubator and the top cover of the shake flask has to be removed, is overcome. In other words, cultivation in conventional shake flasks cannot be performed at constant and hence reproducible environmental conditions as already the necessary removal from the incubator and the opening of the top cover alter these conditions, e.g. in terms of the pH value, the pO2 value, the pCO2 value, the power input, or the temperature and each cell culture only recovers slowly and individually from these abrupt changes. This results in hardly predictable and also non-reproducible metabolic changes of the cultivated cells which in turn result in different overall product yields or product quality. However, via employing the sterilizable adapter culture conditions e.g. in shake flasks become reproducible and comparable for cell culture condition such as batch, fed-batch, repeated fed-batch and/or continuous cultivation conditions e.g. perfusion culture conditions. This is even the case for cell culture on a small scale. Hence, the sterilizable adapter ensures a more efficient process in determining parameters for scale-up while reducing the costs.

In one embodiment, the sterilizable adapter described herein further comprises at least one level sensor.

As used herein the term "level sensor" refers to a measuring transducer that converts the level measurements of liquids into mechanical, electrical, or pneumatic signals that can then be conveniently transmitted, processed, and recorded. The level sensor ensures that the level of liquid in the cell culture vessel, e.g. nutrient solution or cell culture medium, is constant within a range tolerated by the cultured cells under given culture conditions.

The use of a level sensor facilitates small scale cell culture under continuous culture conditions e.g. perfusion culture conditions. This is the case, since small culture volumes always carry the risk that the culture vessel is depleted of or overfilled with liquid. This risk is minimized via monitoring the liquid level.

In case that the liquid level is too low or too high for example in the case of perfusion culture conditions the volumetric flow rate can be adjusted accordingly.

In one embodiment the level sensor is connected to a port.

In another embodiment the level sensor is positioned in the ventilation passage of the sterilizable adapter.

Figure 8:
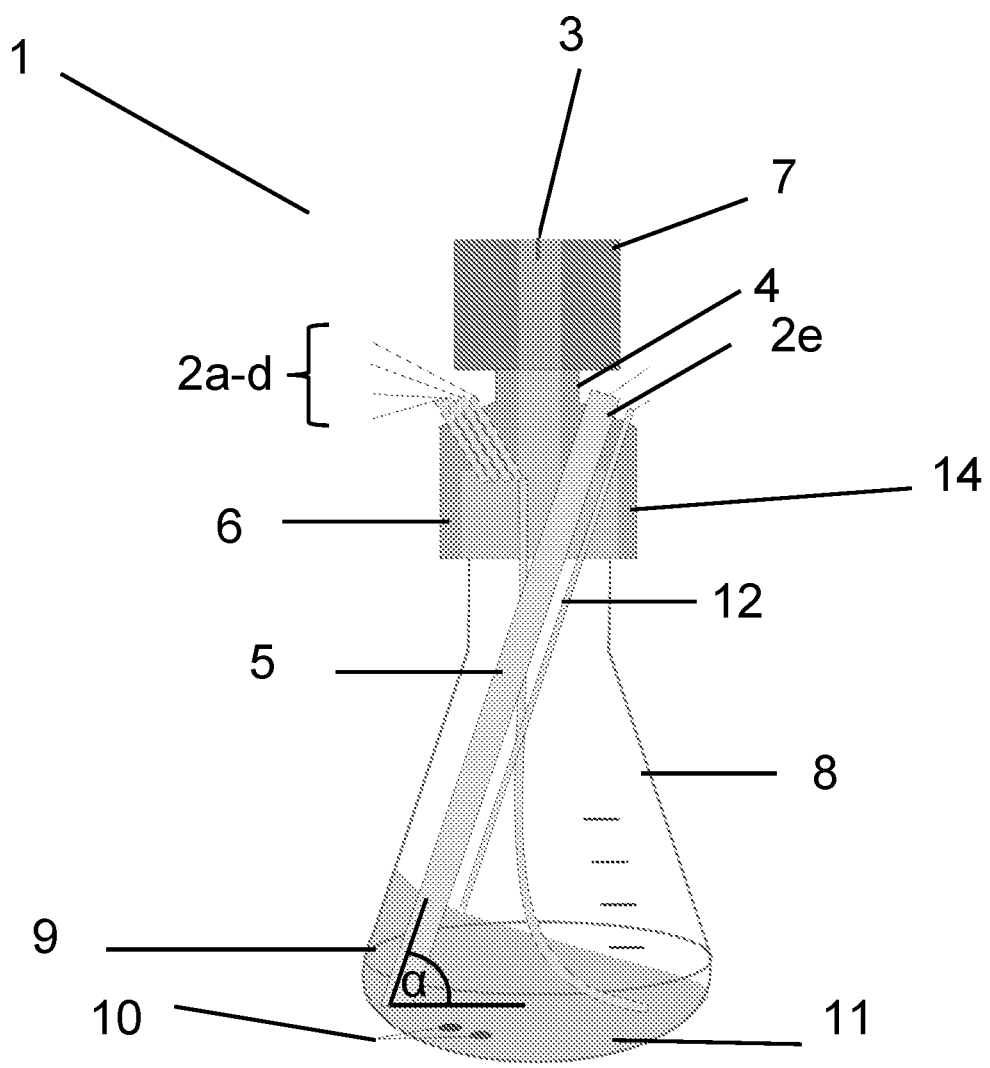
FIG. 8 shows another exemplary device comprising an alternative embodiment of sterilizable adapter compared to FIG. 4 and a cell culture vessel.

In a further embodiment the body of the sterilizable adapter comprises an insertion for a level sensor e.g. via a screw thread and a tight clamp connection (FIG. 8).

In a preferred embodiment the measurement of the liquid level in the cell culture vessel and if necessary the adjustment of the volumetric flow rate in the case of a perfusion culture is performed once a day.

A different way of determining the liquid level is to monitor exactly the substances, which are added and removed from the culture vessel including the liquid samples that are taken during the cultivation. This method can be used in addition or as alternative.

In the case of small-scale culture volumes also a combination of determining the liquid level of the cell culture via monitoring of added and removed substances, employing a level sensor can be employed in order to tightly control liquid levels especially in cases of perfusion culture conditions.

Examples of level sensors are floating, hydrostatic, electric, thermal and optical sensors. These are known in the art.

In a preferred embodiment of the sterilizable adapter described herein it comprises at least one electrode and/or at least one conductive probe as level sensor.

Examples of such level sensors are capacity and conductivity level sensors.

The working principle of a capacity level sensor lies in the fact that an increase in liquid level causes deeper immersion of the measuring electrode and thereby increases its capacity signal. This measured capacity for example sets the output of the level meter.

A conductivity level sensor, on the other hand, evaluates the change in electrical resistance of the measured medium. This could for instance be carried out via evaluating the change of electrical resistance between two conductivity probes or the change of electrical resistance is evaluated between the conductivity probe and another metal object, e.g. the vessel wall or the cell retention device.

Preferably the level sensor monitors the liquid level during cultivation and ensures that the liquid level is constant within a range of ±50% of the desired volume, more preferably within a range of ±10% of the desired volume and most preferably within a range of ±5% of the desired volume.

Hence, if the level is outside this range the conditions are adjusted, e.g. via adding more liquid or removing less liquid.

A preferred conductivity level sensor is the "DASGIP® Levelsensor" from Eppendorf AG, Hamburg, Germany, which has a length of 22 cm and a diameter of 3 mm.

There is no limitation in terms of cell types that can be cultivated using the sterilizable adapter, e.g. it can be used for cultivating microbial cells, mammalian cells, insect cells, yeast cells or plant cells. In other words, the term "cell culture" as used herein, refers to the cultivation of microbial cells, mammalian cells, insect cells, yeast cells or plant cells.

Preferably the cultivated cells are mammalian cells.

Moreover, the sterilizable adapter can not only be used for any type of cell culture but also for any cell culture purpose. A particularly preferred purpose—as mentioned above—is the optimization of cell culture conditions in order to optimize biotechnological processes for example in terms of product yield, product quality or in order to reduce culture costs.

In this context the term "biotechnological" refers to the use of microorganisms or cells such as bacteria, yeasts, insect, plant or mammalian cells to perform specific industrial or manufacturing processes.

A preferred example of an upper connection is an upper external screw thread, since the screw thread facilitates a quick and reliable connection of the sterilizable adapter with a suitable lid for example the lid of a suitable cell culture vessel the adapter is attached to.

The sterilizable adapter can also comprise a lid instead of, or in addition to, the upper connection.

Preferably said lid comprises a membrane allowing gas exchange between the interior of the cell culture vessel and the environment e.g. of a cell incubator.

Depending on the cell culture vessel chosen for a giving experiment, the diameter of the upper connection and/or a lid can vary.

In a preferred embodiment of the sterilizable adapter describe herein the lower internal connection suitable for connection to a cell culture vessel is a screw thread suitable for screwing in a screw thread, as the screw thread facilitates a quick and reliable connection of the sterilizable adapter with a suitable cell culture vessel, which has a corresponding screw thread.

Depending on the cell culture vessel chosen for a given experiment, the diameter of the lower internal connection suitable for connection to a cell culture vessel can vary.

Hence, depending on the cell culture vessel chosen for a given experiment, the diameter and size of the sterilizable adapter can vary in order for the sterilizable adapter to fit to the cell culture vessel and to be suited for the original lid of that given cell culture vessel.

Figure 7:
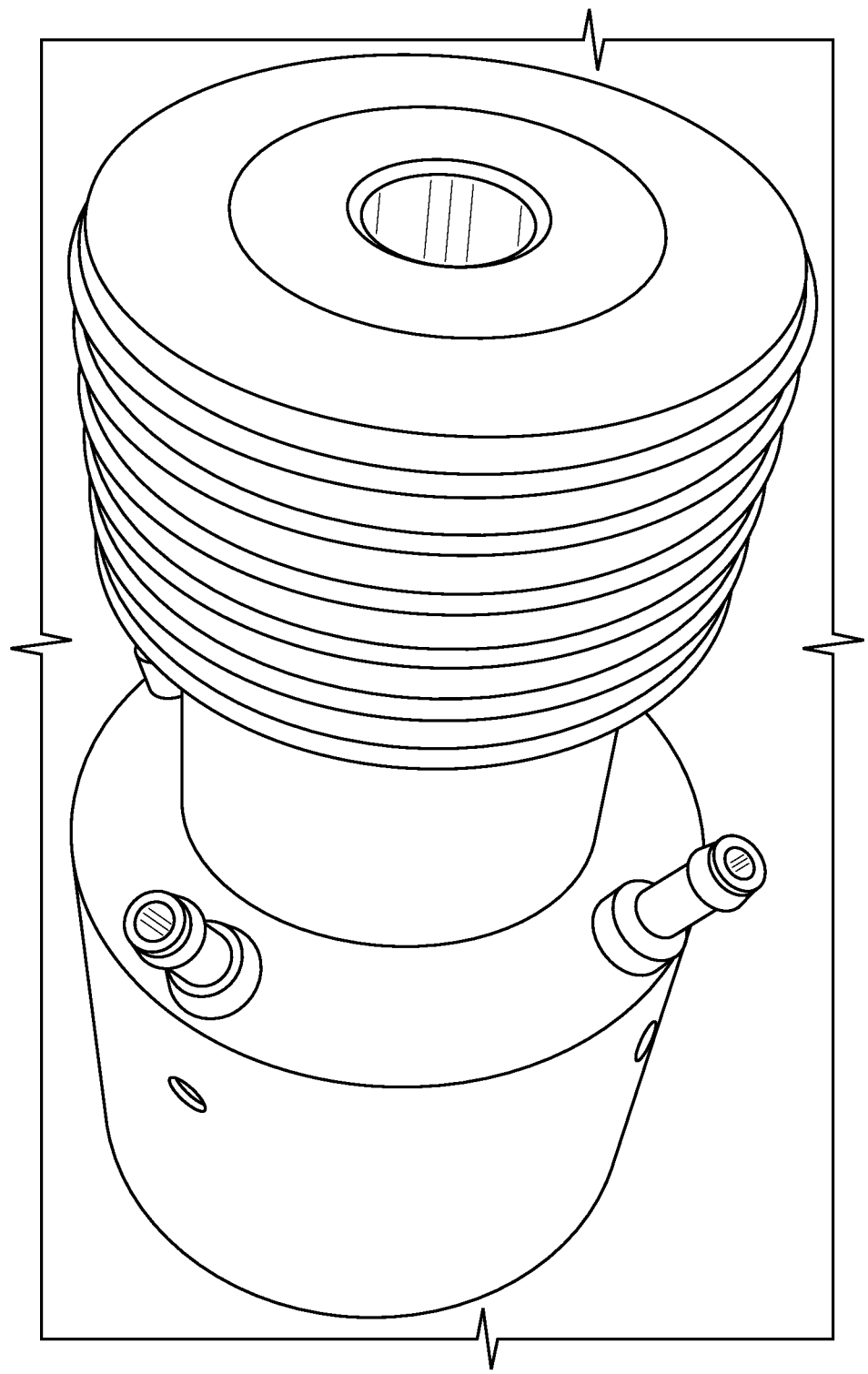
FIG. 7 shows a picture of an exemplary sterilizable adapter.

In one embodiment the sterilizable adapter has a height of 88 mm, a diameter at the top of 42 mm, an outer diameter of 50 mm and an inner diameter of 40 mm at the bottom, 4 ports, each with a length of 46 mm, and an inner diameter of 2 mm as well as a ventilation passage with an inner diameter of 10 mm. This specific embodiment of the sterilizable adapter described herein is depicted in FIG. 7.

The sterilizable adapter can be disposable, i.e. for one time use or can be re-usable.

Moreover, it is possible that during a given experiment the cell culture condition is altered, e.g. the cells are at first cultured under fed-batch conditions followed by cultivation under perfusion conditions.

The employed substances that are added and/or removed via the sterilizable adapter can be in solid, liquid or gaseous state. Preferably, the added or removed substances are liquids or gases.

Referring to the ports of the sterilizable adapter: usually, if a given port serves in a given experiment as inlet for a specific substance, it will not serve as inlet for another substance or as outlet.

However, it is also possible to assign more than one function to a given port, e.g. cell culture medium can be added via a specific port and also cells to be cultured can be added via this port. One way of achieving this is through using a sterilized Y-tube connected to the port, in which one arm of the "Y" is used for adding cell culture medium and one arm for adding cells to be cultured.

If during batch cultivation not all connectors are used, they can be equipped with filters or sealed off.

Preferably, the sterilizable adapter has 2 to 20 ports, more preferably, 2 to 10, even preferably 4 to 8 ports.

In a preferred embodiment of the sterilizable adapter the ports are straight.

Alternatively the ports are bent, e.g. "L" shaped.

In a further preferred embodiment of the sterilizable adapter the ports are positioned vertically or at an incline within the body of the adapter.

Preferably the incline is at an angle of 45°.

In a preferred embodiment the ports of the adapter are straight. Thus, no dead space is present within the port, thus minimizing the risk that added or removed substances remain in the ports. The straight ports can for instance be positioned vertically or at an angle of 45°.

Preferably the ports of the sterilizable adapter have an inner diameter of 1.5-3.5 mm, preferably of 2.3 mm.

In a preferred embodiment the sterilizable adapter has 5 ports. Of these five ports four are of equal dimensions with respect to length and diameter, while the fifth port is configured to allow outlet of the harvest stream via the cell retention device.

This embodiment can be combined with the embodiment described above in which the body of the sterilizable adapter comprises an insertion for a level sensor e.g. via a screw thread and a tight clamp connection. Such a combination results in a sterilizable adapter as depicted in FIG. 8.

Figure 4:
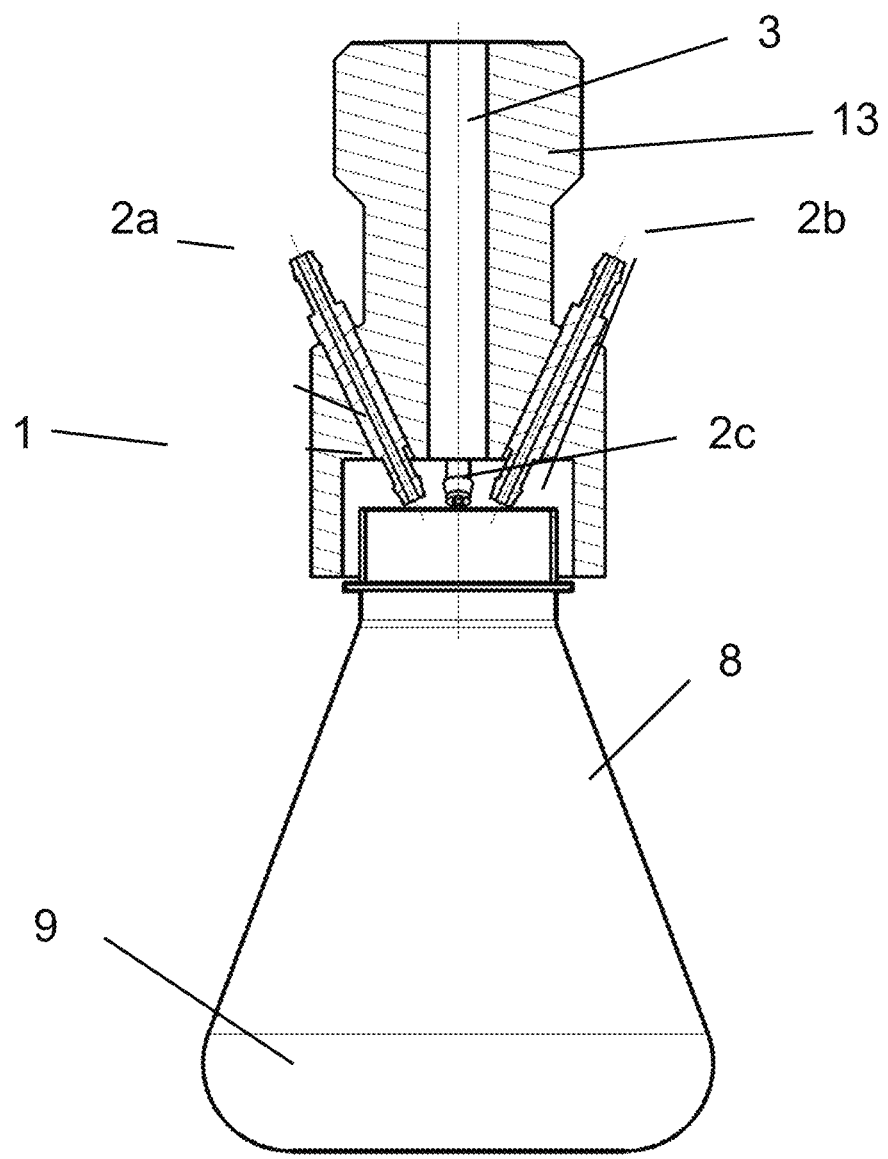
FIG. 4 shows a side-view of the exemplary device of FIG. 3 comprising a sterilizable adapter and a cell culture vessel.

Moreover, the outer diameter of the sterilizable adapter can be smaller at the locations where the ports exit the body of the sterilizable adapter as shown in FIG. 4.

If the sterilizable adapter has more than one port the ports can be arranged at equal distances from each other and/or at the same position relative to the total height of the sterilizable adapter.

In a further preferred embodiment of the sterilizable adapter described herein the cell retention device is connected to the at least one port or the cell retention device is positioned in the ventilation passage of the adapter.

Depending on parameters such as the cultured cell type, the chosen cell culture vessel and the chosen cell culture volume it can be advantageous that the cell retention device is positioned in the ventilation passage of the adapter.

In such an embodiment, the cell retention device is preferably mounted into the lid, which is to be used with the sterilizable adapter, prior to sterilization e.g. autoclaving.

In one embodiment the sterilizable adapter described herein comprises a cell retention device and the inner surface of said cell retention device is modified in order to further enhance the sliding properties of the chosen surface material. If the surface and/or the cell retention device is for example manufactured from stainless steel said modification of the surface can be achieved for example via electropolishing and/or via mirror polishing. If the surface and/or the cell retention device is for example manufactured from glass the glass surface may be modified with respect to its hydrophobic and/or hydrophilic properties. Further methods of modifying the surfaces also of other materials e.g. plastics are known by those skilled in art.

Without wishing to be bound by theory it seems that especially in the case of cell retention devices taking advantage of gravity, i.e. gravity cell settlers, the surface quality of the inner surface influences the rate with which the cells slide down the cell retention device. In other words, the better the sliding properties of the surface the better the cell retention characteristics of a cell retention device taking advantage of gravity.

Thus, in a further preferred embodiment the cell retention device is a gravity cell settler manufactured from stainless steel, has a length of 20 cm to 24 cm, an inner diameter of 8 mm to 12 mm, is inclined with an angle of 70 to 75° with respect to a horizontal line and has an electropolished inner surface.

In a preferred embodiment the sterilizable adapter further comprises at least one component selected from the group consisting of a tube, a filter, a hose nozzle, a screw connector, a luer lock connector and an external cell separation.

Preferably, the hose nozzle is a metal hose nozzle with a length of approx. 5 cm.

In another aspect the present invention provides a device comprising a sterilizable adapter as described above and a cell culture vessel. Moreover, if the adapter does not already comprise a lid, the device preferably comprises a lid.

Examples of such devices are depicted in FIG. 1 and FIG. 8.

In a preferred embodiment the device is suited for a culture volume of 1 ml to 170 ml.

In an especially preferred embodiment the device is suited for culturing high cell densities under perfusion type cell culture conditions in a culture volume of 100 ml to 145 ml.

Preferably the device as a whole or in parts is sterilizable.

Preferably the lid is the lid originally belonging to the cell culture vessel of the device.

Preferably the device further comprises a component selected from the group consisting of: at least one pH sensor spot, a conventional pH electrode, a sensor for optical density, a sensor for dissolved oxygen, a conductivity sensor and/or a capacity sensor.

In yet another aspect the invention relates to the use of sterilizable adapter and/or the device as described above for cultivation of cells under batch, fed-batch, repeated fed-batch and/or continuous such as perfusion culture conditions, wherein in the case of perfusion culture conditions the adapter comprises at least 2 ports.

In the case of a perfusion culture one out of the at least two ports could for example be used to add pH set-up agents and cell culture medium ("feed") and the other one of the at least two ports could be employed to remove cell culture medium ("harvest") and samples could be taken from the harvest stream.

However, in a preferred embodiment of said use the sterilizable adapter comprises at least four ports, since it readily allows culture under perfusion culture conditions.

In another preferred embodiment of said use the sterilizable adapter comprises 5 ports, 4 of which are of equal dimensions with respect to length and diameter and the fifth port is configured to allow outlet of the harvest stream via a cell retention device manufactured from stainless steel with a length of 23.5 cm, an inner diameter of 10 mm and an inclination angle of 74° with respect to a horizontal line.

In a further embodiment of said use the sterilizable adapter comprises 5 ports, one of which is configured to allow outlet of the harvest stream via a cell retention device and one port is used for active headspace aeration thus allowing for optimized cell culture conditions for high cell densities under perfusion conditions.

In yet another embodiment of said use the body of the sterilizable adapter comprises an insertion for a level sensor.

In a further embodiment of said use the cell retention device is positioned in the liquid phase of the cell culture vessel.

Thus, in one example of said use the sterilizable adapter comprises 5 ports, one of which is configured to allow outlet of the harvest stream via a cell retention device, one port is used for active headspace aeration and the cell retention device is positioned in the liquid phase of the cell culture vessel.

In a preferred embodiment of said use the sterilizable adapter and/or the device describe herein are used for a perfusion cell culture under shaking conditions, i.e. constant orbital rotational movement.

In yet another aspect the invention relates to a method for cultivation of cells under batch, fed-batch, repeated fed-batch and/or continuous such as perfusion culture conditions.

In a preferred embodiment of the cell cultivation method the method further comprises detection of the liquid level.

The liquid level can for example be detected via using a capacity sensor or via monitoring the weight balance of the substances that are added to and removed from the cell culture vessel.

Detection of the liquid level facilitates small scale cell culture under continuous culture conditions e.g. perfusion culture conditions. This is the case, since small culture volumes always have the risk that the culture is depleted of or overfilled with cell culture medium. This risk is minimized via monitoring the cell culture medium level.

Moreover, ensuring a constant liquid level also facilitates controlling other culture parameters such as the dissolved oxygen concentration.

In a preferred embodiment of the cell cultivation method the sterilizable adapter comprises at least two ports and the cell cultivation method is a perfusion cell culture.

FIG. 1 shows a schematic overview of a sterilizable adapter and a device comprising such a sterilizable adapter, i.e. a cell culture vessel and a lid as described herein. In detail, a sterilizable adapter (1) for a cell culture vessel (8) is depicted. The sterilizable adapter in this example comprises a body (14), an upper external screw thread (4) four ports (2*a-d*), a ventilation passage (3), an internal screw thread suitable for screwing in a screw thread (6) and a cell retention device (5) taking advantage of gravity. In this example the sterilizable adapter (1) is positioned on a cell culture vessel (8) and it is closed with the original lid (7) of said cell culture vessel. The cell culture vessel contains cell culture medium (9) comprising the cells to be cultured (11). Moreover, the cell culture vessel comprises a pH sensor spot and a dissolved oxygen sensor spot (10) indicating a change in pH value and dissolved oxygen tension.

This sterilizable adapter can be used as follows:

In this example the cell culture vessel (8) is a pre-sterilized 250 ml shake flask comprising a lid, which allows ventilation via a membrane. Moreover, the sterilizable adapter (1) was autoclaved. The function of ports 2*a*-2*d* in this example is as follows: port 2*a* allows for the addition of cells to be cultured, port 2*b* allows for the addition of cell culture medium, port 2*c* allows harvest of the cell culture medium and is hence connected to the cell retention device (5). Finally port 2*d* allows for samples to be taken during the cell cultivation period. Moreover, in this example each port has a metal hose nozzle. Depending on the given requirements sterile tubes and/or filters are added to the ports inside the culture vessel or outside the culture vessel, in order to ensure a sterile culture environment inside the cell culture vessel.

Prior to setting up the cell culture the lid (7) is removed from the shaker flask under sterile conditions. Then, the sterilizable adapter (1) is screwed onto the cell culture vessel via the internal screw thread suitable for screwing in a screw thread (6) and the lid (7) is screwed onto the sterilizable adapter (1). Afterwards the whole device is transferred to the cell cultivation chamber, here an incubator, in which the cells are cultured under suitable conditions in perfusion culture mode.

In the next step 100 ml of the cell culture medium (9) are added via port (2*b*) and the cells to be cultured (11) are added via port (2*a*) to the cell culture vessel (8).

Finally the perfusion cell culture is started, in which culture medium is continuously added via port (2*b*) and aspirated via port (2*c*), while the cell retention device retains the cells to be cultured in the medium.

In this example, the level of the cell culture medium is detected via monitoring the weight balance of the substances that are added to and removed from the cell culture vessel, Overall, using the adapter described herein thus enables cell cultivation as perfusion culture in a small-scale cell culture with 100 ml culture volume.

Figure 2:
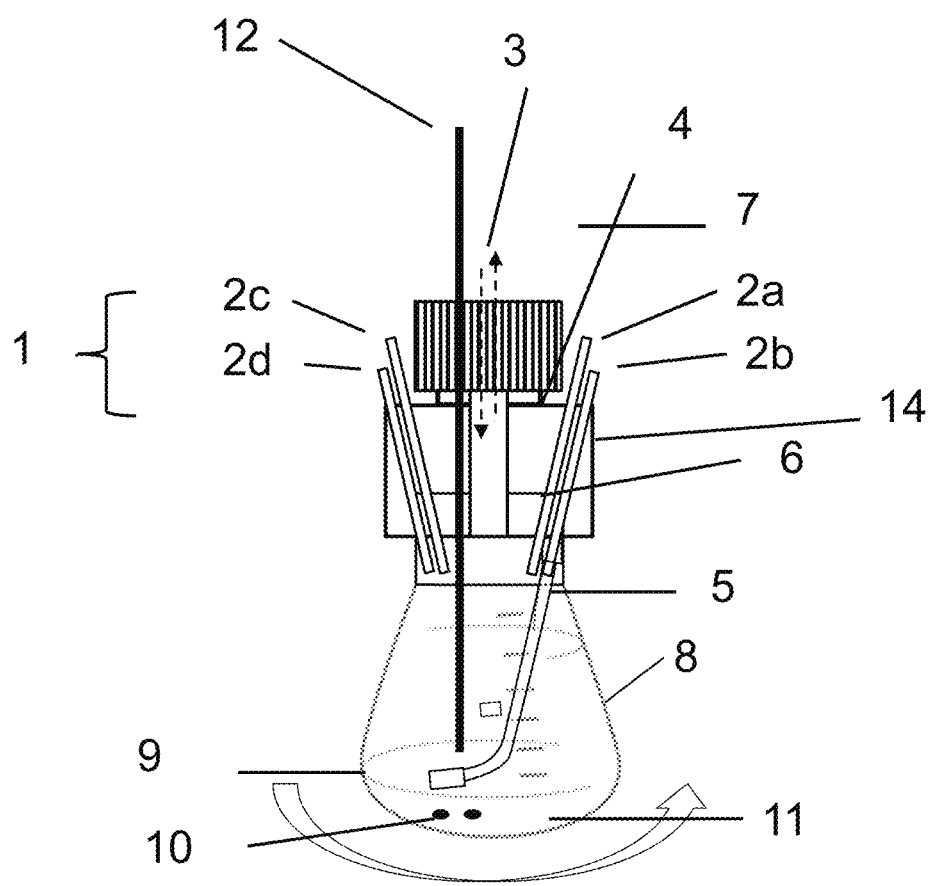
FIG. 2 shows a schematic overview of a sterilizable adapter comprising a level sensor.

FIG. 2 shows a schematic overview of a sterilizable adapter and a device comprising such a sterilizable adapter, i.e. a cell culture vessel and a lid as described herein. In detail, a sterilizable adapter (1) for a cell culture vessel (8) is depicted. The sterilizable adapter in this example comprises a body, an upper external screw thread (4) four ports (2*a-d*), a ventilation passage (3) (gas exchange is indicated by the dashed arrows), an internal screw thread suitable for screwing in a screw thread (6), a cell retention device (5) here a gravity cell settler, a level sensor (12)—in this case a conductivity electrode—and a lid (7). In this example the sterilizable adapter (1) is positioned on a cell culture vessel (8). The cell culture vessel contains cell culture medium (9) comprising the cells to be cultured (11). Moreover, the cell culture vessel comprises pH sensor spots (10) indicating a change in pH value.

Prior to setting up the cell culture the lid (7) with the level sensor (12) is removed from the shake flask under sterile conditions. Then, the sterilizable adapter (1) is screwed onto the cell culture vessel via the internal screw thread suitable for screwing in a screw thread (6) and the lid (7) is screwed onto the sterilizable adapter (1). Afterwards the whole device is transferred to the cell cultivation chamber, here an incubator, in which the cells are cultured under suitable conditions in perfusion culture mode.

In the next step 100 ml of the cell culture medium (9) are added via port (2b) and the cells to be cultured (11) are added via port (2a) to the cell culture vessel (8).

Finally the perfusion cell culture is started, in which culture medium is continuously added via port (2b) and aspirated via port (2c), while the cell retention device retains the cells to be cultured in the medium. In this example, the cell culture vessel (8) is a shake flask and the cells are cultured at 120 rpm (indicated by the semi-circle arrow) in a constant orbital rotational movement.

During cultivation the level of the cell culture medium is monitored via the level sensor (12) and if necessary the conditions are adjusted, e.g. via adding more culture medium or removing less culture medium ensuring that the level of the cell culture medium is constant within a narrow range.

Overall, using the adapter described herein thus enables cell cultivation as perfusion culture in a small-scale cell culture with 100 ml culture volume.

Figure 3:
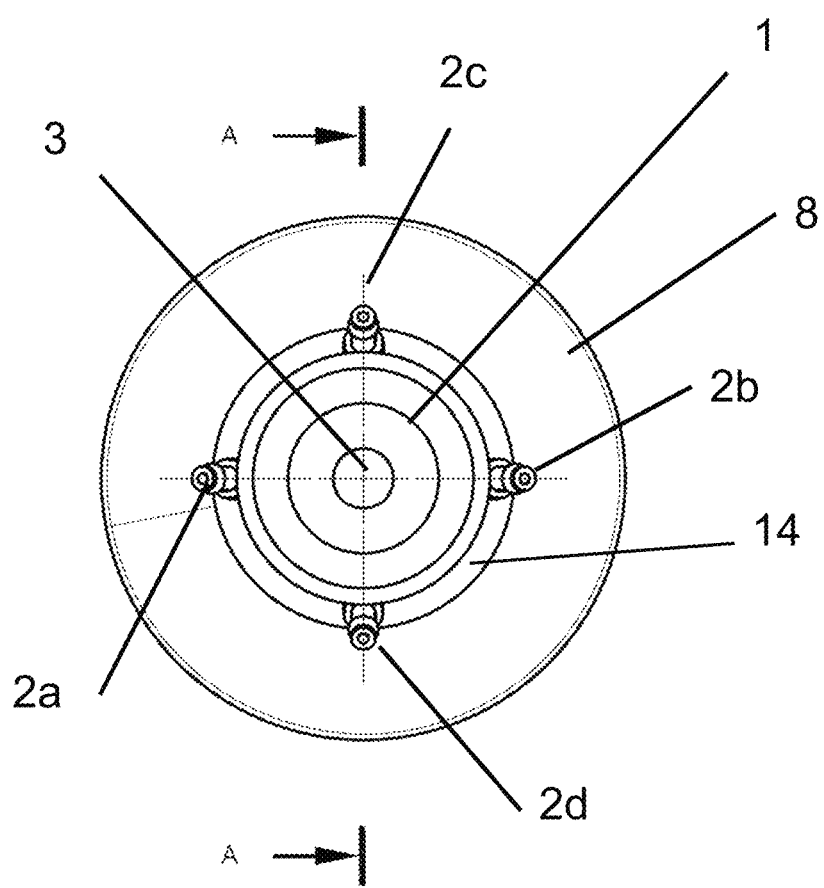
FIG. 3 shows an exemplary sterilizable adapter from above.

FIG. 3 shows an exemplary device comprising a sterilizable adapter and a cell culture vessel from above.

In detail, a sterilizable adapter (1) for a cell culture vessel (8) is depicted. Moreover, also the four ports (2a-d), the ventilation passage (3) and the body of the adapter (14) are shown. In addition, in this example of a sterilizable adapter, the four ports are arranged at equal distances from each other.

FIG. 4 shows a side-view of an exemplary device comprising a sterilizable adapter and a cell culture vessel.

In detail, a sterilizable adapter (1) for a cell culture vessel (8) is depicted. In this view, only the three ports 2a-c are shown, as the fourth ports located on the visual axis, since in this example of a sterilizable adapter, the four ports are arranged at equal distances from each other. In addition the four ports are also arranged at the same position relative to the total height of the sterilizable adapter. In this example, the ports end at the top of the cell culture vessel (8) and do not extend into the cell culture vessel (8) as is the case in the exemplary device depicted in FIG. 2. Moreover, also the ventilation passage (3), the body (13) and the cell culture medium (9) comprising the cells to be cultured are depicted.

Figure 5:
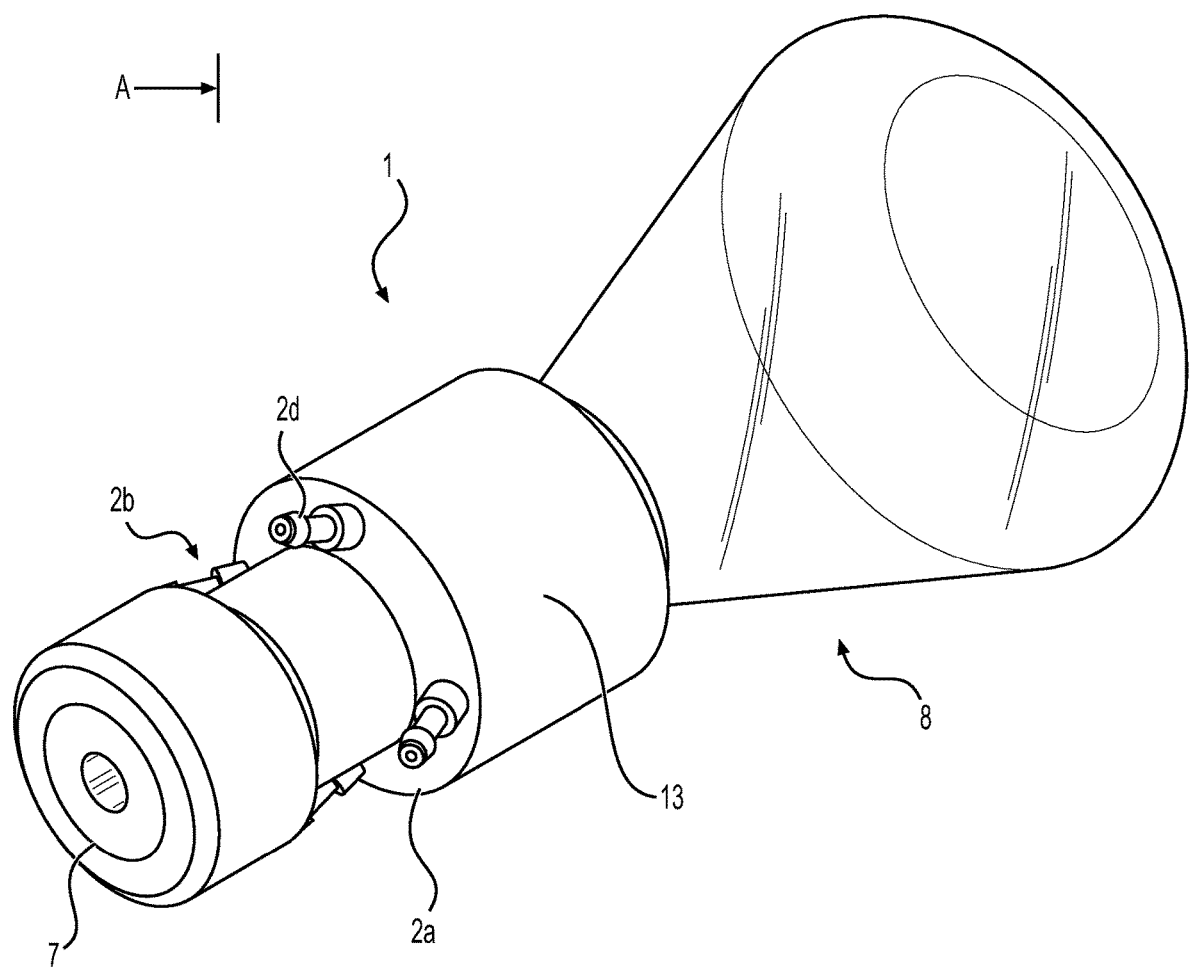
FIG. 5 shows another view of an exemplary device comprising a sterilizable adapter and a cell culture vessel.

FIG. 5 shows another view of an exemplary device comprising a sterilizable adapter and a cell culture vessel. Depicted are a sterilizable adapter (1) for a cell culture vessel (8) comprising a body (13) and a lid (7) for the sterilizable adapter, which in the example is the original lid of the cell culture vessel. In this view, the three ports ports 2a, 2b and 2d are depicted.

Figure 6:
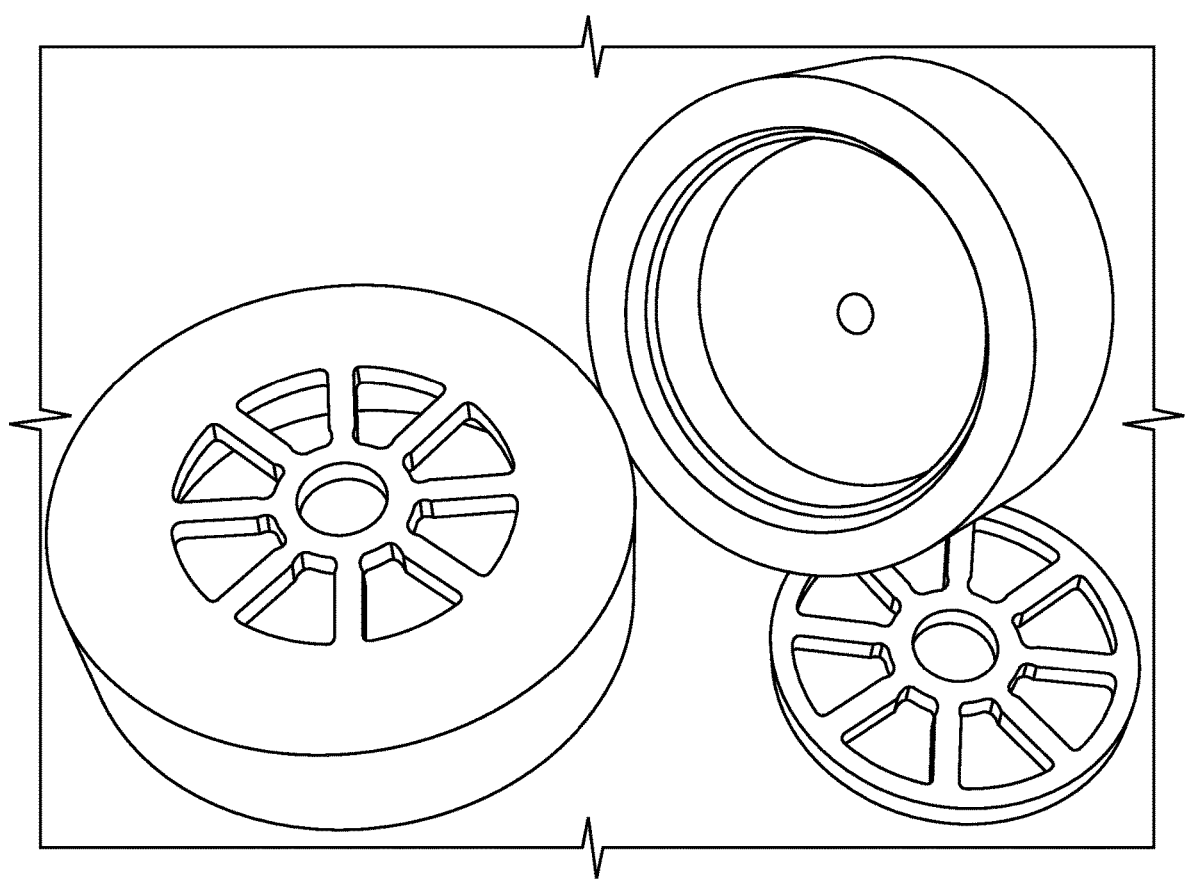
FIG. 6 shows a picture of an exemplary cell retention device, i.e. a filtration membrane.

FIG. 6 shows a picture of an exemplary cell retention device, i.e. a filtration body. It consists of two parts between which the filtration material was placed. For stabilization of the filtration material a stabilization disk was also placed into the filtration body. The employed filtration material was a 20 μm prefilter and a 10 μm-filter material, i.e. a super micron filter.

FIG. 7 shows a picture of an exemplary sterilizable adapter comprising as an upper connection a screw thread and four ports of which two can be seen.

FIG. 8 shows another exemplary device comprising a sterilizable adapter and a cell culture vessel.

In detail, a sterilizable adapter (1) for a cell culture vessel (8) is depicted. The sterilizable adapter in this example comprised a body (14), an upper external screw thread, five ports (2a-e), a ventilation passage (3), an internal screw thread suitable for screwing in a screw thread (6), a level sensor (12)—in this case a conductivity electrode—and a cell retention device, here a gravity cell settler (5), which was inclined 74° with respect to a horizontal line (angle α). In this example the sterilizable adapter (1) was positioned on a cell culture vessel (8)—here a shake flask—and it was closed with the original lid (7) of said cell culture vessel via an upper external screw thread (4). The cell culture vessel contained cell culture medium (9) comprising the cells to be cultured (11). Moreover, the cell culture vessel comprised a pH sensor spot and a dissolved oxygen sensor spot (10) indicating a change in pH value and dissolved oxygen tension.

In this example the functions assigned to first four ports (2a-d), which are of equal dimensions with respect to length and diameter, were
1) sampling and inoculation,
2) feed addition
3) base addition
4) active headspace aeration A further port (2e) was configured to allow outlet of the harvest stream via the cell retention device (5).

Moreover, in this example the body (14) of the sterilizable adapter comprised an insertion for a level sensor (12) via a screw thread and a tight clamp connection.

Since the sterilizable adapter in this example comprised a lid (7) with a membrane allowing gas exchange between the interior of the cell culture vessel and the environment, outlet gas was released via said membrane to maintain a contained cultivation environment inside of the cultivation flask In addition the supplied air was filtered with a 0.2 μm filter.

Figure 9:
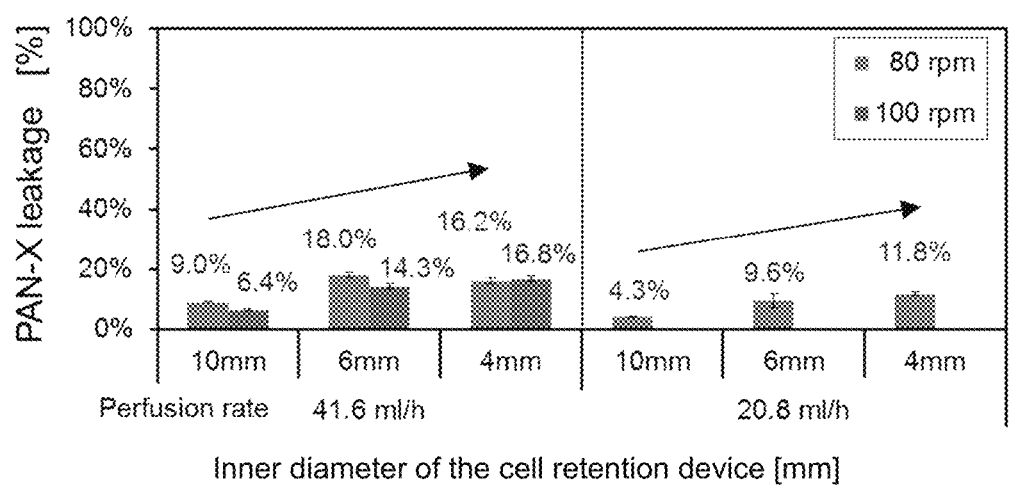
FIG. 9 shows an overview over the PAN-X leakage values for perfusion rates of 20.8 mL/h and 41.6 mL/h determined for cell retention devices with inner diameters of 4 mm, 6 mm and 10 mm

FIG. 9 shows the result of an experiment with polyacrylonitrile particles (PAN-X)

Analog to the term $k_{Wash}$ that is used to specify the percentage of viable cells lost in harvest, the particle leakage [%] was used to specify the amount of particles in the harvest line in relation to the amount of particles in the reactor system. A different term was used because the values for particle leakage are not directly comparable with the values for $k_{Wash}$. In detail, PAN-X leakage [%] for perfusion rates of 41.6 mL/h and 20.8 mL/h was determined for inclined (74°) cell retention devices with inner diameters of 4 mm, 6 mm and 10 mm in the perfusion bioreactor system shown in FIG. 8.

Figure 10:
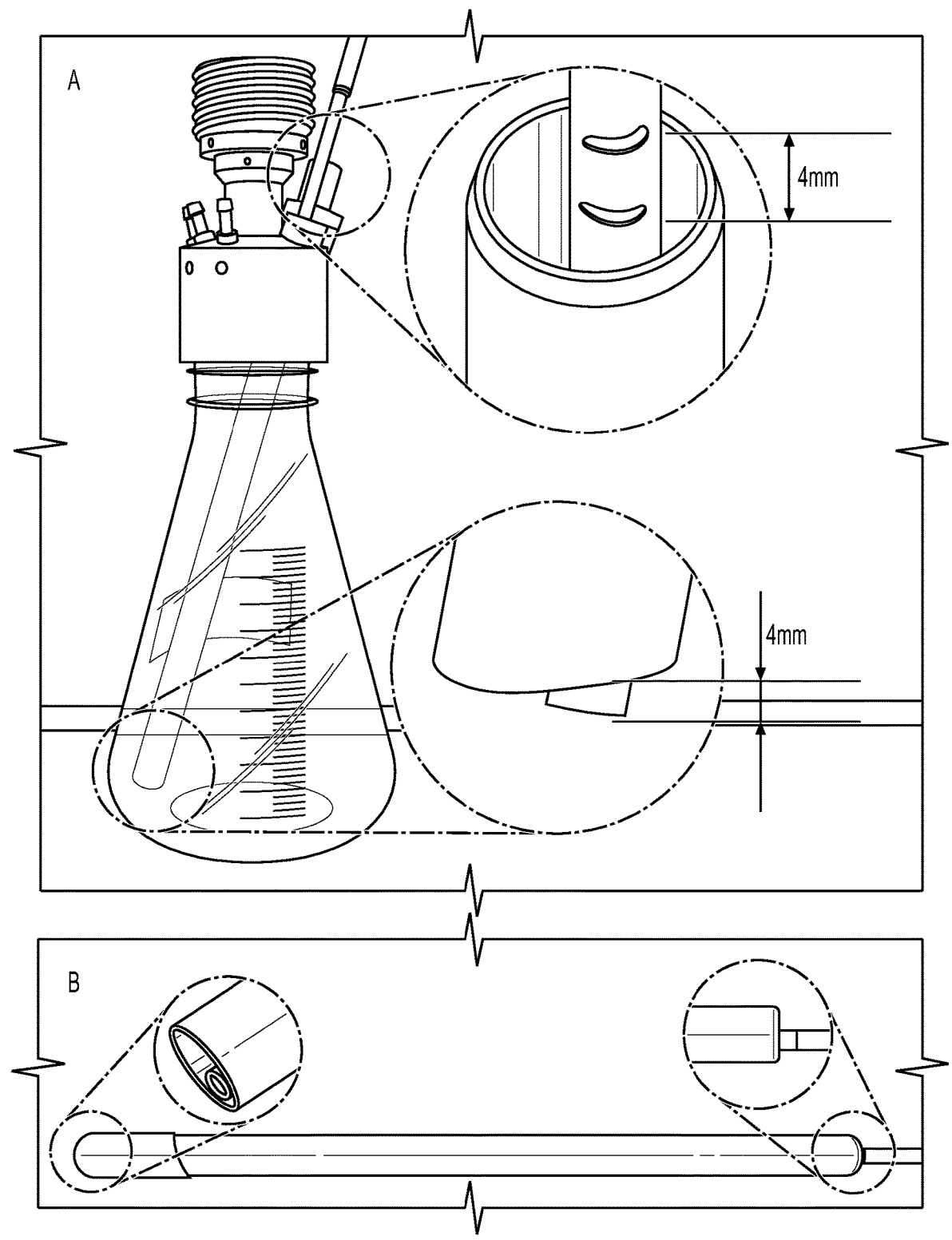
FIG. 10 shows an illustration of an exemplary installation of the cell retention device.

FIG. 10 shows an illustration of the installation of a cell retention device in form of a gravity cell settler.

EXAMPLES

Example 1 Initial Experiments

The device of FIG. 4 comprising the sterilizable adapter was tested under perfusion culture conditions. In detail, the employed sterilizable adapter had as upper connection, an upper external screw thread to which the original lid of the cell culture vessel was screwed onto and as lower internal connection a screw thread via which the adapter was screwed onto the cell culture vessel. In addition, the sterilizable adapter had 4 straight, vertically positioned ports, a ventilation passage, a level sensor and a cell retention device, here a gravity cell settler, in this case a piece of elastomeric tubing. The cell retention device was connected to one of the ports. Moreover, the ports were fitted with components such as tubes, filters, hose nozzles, screw connector and luer lock connectors as appropriate.

Prior to use the sterilizable adapter was sterilized via steam sterilization. Afterwards the cell retention device was screwed onto the cell cultivation device and the other components were assembled under a sterile workbench (cleanbench).

In this example of the described sterilizable adapter human recombinant blood-clotting factor VIII (rFVIII) expressing baby hamster kidney (BHK) cells were cultured for several weeks. The culture conditions were set at an incubator temperature of 36.5° C.—and a shaking frequency of the incubators shaking platform of 100 rounds per minute (rpm)—which was adjusted to 120 rpm after a while—in order to increase the oxygen transfer. Moreover, the CO2-level of the incubator was set at 4.5%, the humidity level of the incubator was set at 80% and the liquid level, i.e. the fill level of the cell culture vessel, was set at 150 ml. Furthermore, at the start the pH set point was 7.0—which was adjusted to pH 6.8 after a while.

The culture was performed in an incubator comprising a shaking platform for cell culture vessels using a DASGIP®-fermenter control including a DASGIP®-control-software (DASGIP®, Eppendorf AG, Hamburg, Germany).

The results showed that via employing the sterilizable adapter described herein cell culture under perfusion culture conditions is possible on a small scale and that the generated metabolite data (data not shown) is comparable to data of production fermenters.

Example 2 Assessment of Different Cell Retention Devices

In a different experiment various pieces of tubing, which differed in length and forms as shown in Table 1, were tested as cell retention devices.

TABLE 1

| | Material | Length Form |
|---|---|---|
| 1 | Silicone, inner diameter 4.8 mm | 163 mm Straight, vertical |
| 2 | Silicone, inner diameter 4.8 mm | 125 mm Straight, vertical |
| 3 | Silicone, inner diameter 4.8 mm | 200 mm Straight, vertical |
| 4 | Silicone, inner diameter 4.8 mm | 200 mm Bent |
| 5 | Tygon ® inner diameter 4.8 mm | 163 mm Straight |
| 6 | Stainless steel, inner diameter 3 mm | 300 mm Straight, 70° inclined* |
| 7 | Stainless steel, inner diameter 4 mm | 300 mm Straight, 70° inclined* |
| 8 | Stainless steel, inner diameter 6 mm | 300 mm Straight, 70° inclined* |
| 9 | Stainless steel, inner diameter 10 mm | 300 mm Straight, 70° inclined* |

*70° inclined with respect to a horizontal line

In this example rFVIII expressing BHK cells were cultured for several days. Cell culture was performed in 500 ml shake flasks with a working volume of 150 ml. The culture conditions were set to an incubator temperature of 36.5° C. and a shaking frequency of the incubator of 80 to 100 rounds per minute (rpm). Moreover, the CO2-level of the incubator was set at 4.5% and the humidity level of the incubator was set at 80%. Furthermore, the pH set point was 6.8 and the dissolved oxygen concentration was >10%.

The results demonstrated that in this setting the straight and 70° inclined stainless steel tube with an inner diameter of 4.86 mm and a length of 300 mm gave especially good results with respect to cell retention.

Example 3—Further Evaluation of Different Cell Retention Devices Especially for High Cell Densities In order to further evaluate which geometries of cell retention devices taking advantage of gravity might be especially suited for obtaining and maintaining high density cell cultures, a polyacrylonitrile particle (PAN-X) system was used. The physical parameters of this PAN-X particle system were determined before the system was used for the evaluation of the performance of the cell retention devices (data not shown).

Several geometries of cell retention devices were investigated with regard to their leakage values. High leakage values indicate that many PAN-X particles are washed out.

Surprisingly, it was found that the inclined cell retention device with an inner diameter of 10 mm reached leakage values below 5% (FIG. 9) under shaking culture conditions. This finding was unexpected since—without wishing to be bound by theory—it was expected that the constant orbital rotational movement of the shake flask would interfere with sedimentation and hence it would not be possible to reach small leakage values.

Example 4—Evaluation of Different Cell Retention Devices in Form of Gravity Cell Settlers During Perfusion Cell Culture To assess the sterilizable adapter described herein in terms of functionality, sterility and practicability a cultivation run was performed with three different cell retention device geometries. Each cell retention device geometry was tested in duplicate to evaluate the following characteristics of the system:
 cell retention performance of the cell retention device
 suitability of the cultivation system for long-term sterile operation,
 oxygen transfer capability of the reactor with cell retention device,
 accuracy of the level control system with a conductivity probe as level sensor,
 functionality of the pH control system using optical sensor spots.

Thus, six sterilizable adapters were constructed. Each was equipped with 5 ports, to which to following functions were assigned:
 1. sampling and inoculation,
 2. feed addition
 3. base addition
 4. aeration
 5. cell retention/harvest In this example the port for the cell retention device comprised a bore which in turn comprised an insert for inserting the cell retention device, here a screw thread. After insertion—i.e. screwing in—the cell retention device was fixed with two screws: one for fixation around the outer diameter of the cell retention device and one for the downward fixation of the cell retention device. The port had an outer diameter of 15 mm, while the cell retention device had an outer diameter of 12 mm.

Moreover, in this example the body of the sterilizable adapter comprised an insertion for a level sensor—here an integrated conductivity probe for level control—via a screw thread and a tight clamp connection. The cell retention device was used as second electrode in combination with the conductivity sensor to allow a control of the filling level.

The outlet gas was released via a membrane on the lid of the sterilizable adapter to maintain a contained cultivation environment inside of the cultivation flask Three stainless steel cell retention devices with a length of 23.5 cm and an inclination angle of 74° with respect to a horizontal line, which differed in their inner diameter were tested in duplicates.

A complete assembly of a shake flask and a sterilizable adapter comprising the respective cell retention device as well as the components for cell culture medium in- and outflow as well as level control, pH control, base addition and oxygen transfer is in the following referred to as unit.

The aeration of a unit—initially realized by passive gas exchange via the membrane of the sterilizable adapter—was switched to active headspace aeration after a cultivation time of seven days. The combined desired cultivation volume of cell retention device and cell culture vessel was 140 ml. The pH was controlled solely by adjusting the CO2 concentration in the inlet gas.

No contamination occurred during the total cultivation period of 23 days.

The cell retention performance was assessed by the viable cell density (VCD) and the $k_{wash}$ values that were determined during cultivation (data not shown).

The VCD in the later stages of the cultivation is a good indicator for the cell retention performance. During that time the cell load in the cell retention device reached maximum values due to the high cell density in the shake flask. If the cell retention performance during perfusion is not sufficient, cells are washed out of the culture vessel and the cell density declines. This effect was clearly visible for cell retention devices with an internal diameter of 4 and 6 mm. The VCD in these units first increased up to a certain level of cell density and then decreased again. None of these units were able to reach the critical cell density of $20 \times 10^6$ cells/ml. In contrast, the two units that were equipped with cell retention devices with an inner diameter of 10 mm, the critical VCD of $20 \times 10^6$ cells/ml was exceeded and remained constant at approximately $25 \times 10^6$ cells/ml for a duration of more than 10 days. Hence via employing the cell retention devices with an inner diameter of 10 mm it was possible to obtain and maintain cell densities that are comparable to cell densities reached in production bioreactors.

In other words, the unexpected results of the PAN-X experiments could be confirmed and even exceeded the expectations under cell culture conditions as this is the first time that a small scale perfusion system was demonstrated to reach high cell densities during perfusion culture conditions, i.e. during truly continuous operation.

Thus, surprisingly the sterilizable adapter described herein, comprising a relatively simple cell retention device, is suited for retaining cells under perfusion culture conditions during constant orbital rotational movement and even allows obtaining and maintaining high cell densities under these conditions.

Moreover, an exact positioning of the cell retention device seems to have the effect that the cell cultivation method is optimized. Without wishing to be bound by theory, this finding is thought to be due to the fact that a positioning of the cell retention device in the liquid phase of the culture vessel minimizes or prevents gas bubbles from entering the cell retention device, which might otherwise interfere with cell sedimentation.

In order to exactly position the cell retention device in the culture vessel, the device was mounted with a gap of 4 mm to the inner ring of the shake flask bottom as shown in FIG. 10. The positioning was carried out with a measuring rod (cf. FIG. 10). The cell retention device was finally fixed by tightening the screws of the clamp.

Example 5—Evaluation of Comparability of the Small Scale Cultures Attributes to Those in Conventional Bioreactors The results of the above described cell culture experiments were used to specify the optimal design of the cell culture adapter for obtaining and maintaining high cell densities. The second set of cell cultivation experiments was performed with 8 identical cell retention devices (gravity cell settlers) and focused on the evaluation of the comparability between the 8 identical cultures and the comparability of cell culture performance attributes to larger scale cell cultures in conventional bioreactors During the second cultivation run, only active headspace aeration was used for the ventilation of the flasks. In contrast to the first cultivation, only cell retention devices with an inner diameter of 10 mm were used.

To reduce the variation of the filling volume, the thresholds of the level sensor were optimized to 100 µS and 200 µS. With these settings the difference between maximum and minimum filling volume was only 7%. Additionally the mounting of the level sensor was stabilized with a second O-ring in addition to the O-ring used conventionally. This resulted in an improved accuracy of the average filling volume of 104 ml. With these conductivity thresholds and the stable level sensor mounting the deviation of the filling volume and the absolute filling volume were optimized.

Overall the results demonstrated that all cultivation units were able to reach viable cell densities over $20 \times 10^6$ cells/ml and it was shown that in general the small scale cultures attributes generated in these experiments are comparable to those in conventional bioreactors.

In other words a device comprising the sterilizable adapter described herein allows a faster, more efficient and cost reduced process-development with the functionality of a fully equipped bioreactor in terms of process control, feeding, sampling and monitoring.

REFERENCES

Meier et al. (2014) Quasi-continuous fermentation in a reverse-flow diafiltration bioreactor, Biochemical Engineering Journal, Volume 91, 15 Oct. 2014, Pages 265-275
WO2013124326 A1
WO2013124329 A1

The invention claimed is:

1. A sterilizable adapter for a small-scale cell culture vessel comprising:
 a body, an upper connection and/or a lid,
 at least one port for medium addition,
 at least one second port for medium removal,
 a ventilation passage,
 a lower internal connection suitable for connection to the cell culture vessel and
 at least one cell retention device, wherein the cell culture vessel is a shake flask configured to removably receive the sterilizable adapter and the sterilizable adapter is a sterilizable adapter for a small-scale cell culture, with a cultivation volume of 1 ml to 500 ml, wherein the at least one cell retention device is a gravity cell settler and is inclined with an angle between 60° and 80° with respect to a horizontal line;

and wherein the shake flask and adapter in use may be moved by constant orbital rotational movement at a rate of from 100 to 500 revolutions per minute.

2. The sterilizable adapter for a cell culture vessel according to claim 1, further comprising at least one cell culture level sensor extending downwardly from the adapter toward a base of the shake flask such that the cell culture level sensor is about perpendicular to the horizontal line.

3. The sterilizable adapter for a cell culture vessel according to claim 1, wherein the upper connection is an upper external screw thread and/or the lower internal connection suitable for connection to a cell culture vessel is a screw thread suitable for screwing in a screw thread.

4. The sterilizable adapter for a cell culture vessel according to claim 1, wherein the at least one cell retention device is connected to at least one port.

5. The sterilizable adapter for a cell culture vessel according to claim 1, wherein the at least one cell retention device is positioned in a liquid phase of the cell culture vessel.

6. The sterilizable adapter for a cell culture vessel according to claim 1, wherein the at least one cell retention device is inclined with an angle between 70° and 75° with respect to a horizontal line.

7. The sterilizable adapter for a cell culture vessel according to claim 1 wherein the shake flask is an Erlenmeyer flask.

8. An article comprising the adapter of claim 1 removably mounted on a shake flask.

9. A shake flask comprising the sterilizable adapter of claim 1.

* * * * *